US010786528B2

(12) United States Patent
Fitton et al.

(10) Patent No.: US 10,786,528 B2
(45) Date of Patent: Sep. 29, 2020

(54) ANTI-VIRAL FORMULATIONS

(76) Inventors: Helen Fitton, Cambridge (AU); Vicki Gardiner, Cambridge (AU)

(*) Notice: Subject to any disclaimer, the term of this patent is extended or adjusted under 35 U.S.C. 154(b) by 287 days.

(21) Appl. No.: 13/580,502

(22) PCT Filed: Feb. 21, 2011

(86) PCT No.: PCT/AU2011/000180

§ 371 (c)(1), (2), (4) Date: Sep. 20, 2012

(87) PCT Pub. No.: WO2011/100805
PCT Pub. Date: Aug. 25, 2011

(65) Prior Publication Data
US 2013/0065851 A1 Mar. 14, 2013

Related U.S. Application Data

(60) Provisional application No. 61/306,910, filed on Feb. 22, 2010.

(51) Int. Cl.
| | |
|---|---|
| *A61K 31/737* | (2006.01) |
| *A61K 31/215* | (2006.01) |
| *A61K 31/04* | (2006.01) |
| *A61K 31/351* | (2006.01) |
| *A23L 3/3562* | (2006.01) |
| *A23L 3/3535* | (2006.01) |
| *A61K 36/03* | (2006.01) |

(52) U.S. Cl.
CPC .......... *A61K 31/737* (2013.01); *A23L 3/3535* (2013.01); *A23L 3/3562* (2013.01); *A61K 31/04* (2013.01); *A61K 31/215* (2013.01); *A61K 31/351* (2013.01); *A61K 36/03* (2013.01)

(58) Field of Classification Search
CPC .... A61K 31/737; A61K 31/04; A61K 31/215; A61K 31/351; A61K 36/03; A61K 2300/00; A23L 3/3535; A23L 3/3562

USPC ...................................................... 514/54, 56

See application file for complete search history.

(56) References Cited

U.S. PATENT DOCUMENTS

| | | | | |
|---|---|---|---|---|
| 2009/0105190 A1* | 4/2009 | Hatano ................ | A61K 31/737 514/54 | |

FOREIGN PATENT DOCUMENTS

| | | | | |
|---|---|---|---|---|
| EP | 0497341 | A2 | | 8/1992 |
| JP | 2002265370 | A | * | 9/2002 |
| JP | 2008063241 | | * | 3/2008 |
| WO | WO-2004014400 | A1 | | 2/2004 |
| WO | WO-2009027057 | A1 | | 3/2009 |

OTHER PUBLICATIONS

Abe et al.; JP 2008063241 A; Mar. 21, 2008 (Machine-English translation).*
Suetsuna; JP 2002265370 A; Sep. 18, 2002 (Machine-English translation).*
Wang et al. (International journal of biological macromolecules, (Jan. 1, 2010) vol. 46, No. 1, pp. 6-12. Electronic Publication Date: Oct. 31, 2009).*
Makarenkova, et al., "Antiviral Activity of Sulfated Polysaccharide From The Brown Algae *Laminaria japonica* Against Avian Influenza (H5N1) Virus Infection in The Cultured Cells", Voprosy Virusologii/Problems of Virology, Moscow, RU, vol. 55, No. 1, Jan. 1, 2010 (Jan. 1, 2010), pp. 41-45, XP009149956, ISSN: 0507-4088.
Database Medline [Online], US National Library of Medicine (NLM), Bethseda, MD, US; Jan. 2008, Hayashi Toshimitsu: "[Studies on evaluation of natural products for antiviral effects and their applications]", XP002699459, Database accession No. NLM18176057; and Yakugaku Zasshi: Journal of the Pharmaceutical Society of Japan, Jan. 2008, vol. 128, No. 1, Jan. 2008, pp. 61-79; ISSN: 0031-6903.
Database WPI, Week 200965 Thomson Scientific, London, GB; AN 2009-P25744, XP002699499, & JP 2009 221133 A (Daiichi Yakuhin Kogyo KK) Oct. 1, 2009.
Database WPI, Week 200932 Thomson Scientific, London, GB; AN 2009-G75265, XP002699461, & CN 101 385 740 A (Univ Fuzhou) Mar. 18, 2009.
Database WPI, Wook 200932 Thomson Scientific, London, GB; AN 2009-G75190, XP002699462, & CN 101 385 741 A (Univ Fuzhou) Mar. 18, 2009.
Hashimoto, et al., "Antiviral Activity of a Sulphated Polysaccharide Extracted from the Marine Pseudomonas and Marine Plant Dinoflagellata Against Human Immunodeficiency Viruses and Other Enveloped Viruses", Antiviral Chemisty and Chemotherapy, Blackwell Scientific Publ., London, GB, vol. 7, No. 4, Jan. 1, 1996, pp. 189-196, XP009076780, ISSN: 0956-3202.
Hasui, Et Al., "In Vitro Antiviral Activities of Sulfated Polysaccharides From a Marine Microalga (*Cochlodinium polykrikoides*) Against Human Immunodeficiency Virus and Other Enveloped Viruses", International Journal of Biological Macromolecules, Elsevier BV, NL, vol. 17, No. 5, Oct. 1, 1995, pp. 293-297, XP002385558, ISSN: 0141-8130, DOI: 10.1016/0141-8130(95)98157-T.
Database WPI, Week 200519 Thomson Scientific, London, GB; AN 2005-173758, XP002699463, & CN 1 552 346 A (Univ Fuzhou) Dec. 8, 2004.
Database WPI, Week 200851 Thomson Scientific, London, GB; AN 2008-H94090, XP002699466, & CN 101 108 200 A (Zhu G) Jan. 23, 2008.

(Continued)

*Primary Examiner* — Shaojia A Jiang
*Assistant Examiner* — Michael C Henry

(57) ABSTRACT

The present disclosure relates generally to the field of anti-viral therapy and prophylaxis. Formulations and agents are provided which inhibit viruses of the Orthomyxoviridae family and ameliorate symptoms and conditions caused by viral infection. The present disclosure teaches the control of influenza virus infection and spread and amelioration of conditions caused thereby. The formulations and agents may be processed as medicaments or as health supplements for more general application such as in the form of consumer goods or consumer foods.

3 Claims, No Drawings

(56) References Cited

OTHER PUBLICATIONS

Hayashi, et al., "Calcium Spirulan, An Inhibitor of Enveloped Virus Replication, From a Blue-Green Alga *Spirulina platensis*", Journal of Natural Products, American Chemical Socieity, US, vol. 59, No. 1, Jan. 1, 1996, pp. 83-87, XP001055143, ISSN: 0163-3864, DOI: 10.1021/NP960017O.
Database Medline [Online], US National Library of Medicine (NLM), Bethesda, MD, US; Oct. 2006, Lee, et al., "Antiviral Sulfated Polysaccharide From Navicula Directa, A Diatom Collected From Deep-Sea Water in Toyama Bay", XP002699467, Database Accession No. NLM17015966; & Biological & Pharmaceutical Bulletin, Oct. 2006, vol. 29, No. 10, Oct. 2006, pp. 2135-2139, ISSN: 0918-6158.
Hosoya, et al., "Comparative Inhibitory Effects of Various Nucleoside and Nonnucleoside Analogues on Replication of Influenza Virus Types A and B In Vitro and In Ovo", Journal of Infectious Disesases, University of Chicago Press,Chicago, IL, vol. 168, No. 3, Sep. 1, 1993, pp. 641-646, XP000984073, ISSN: 0022-1899.

* cited by examiner

ANTI-VIRAL FORMULATIONS

CROSS-REFERENCE TO RELATED APPLICATIONS

This application is a U. S. National Stage of International Application No. PCT/AU2011/000180, filed Feb. 21, 2011 and published in English as WO/2011/100805 on Aug. 25, 2011. This application claims the benefit of U.S. Provisional Application No. 61/306,910, filed Feb. 22, 2010. The disclosures of the above applications are incorporated herein by reference.

FILING DATA

This application is associated with and claims priority from U.S. Provisional Patent Application No. 61/306,910, filed on 22 Feb. 2010, entitled "Anti-viral formulations", the entire contents of which, are incorporated herein by reference.

FIELD

The present disclosure relates generally to the field of anti-viral therapy and prophylaxis. Formulations and agents are provided which inhibit viruses of the Orthomyxoviridae family and ameliorate symptoms and conditions caused by viral infection. The present disclosure teaches the control of influenza virus infection and spread and amelioration of conditions caused thereby. The formulations and agents may be processed as medicaments or as health supplements for more general application such as in the form of consumer goods or consumer foods.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

The Orthomyxoviridae is a family of RNA viruses which include the genera, Influenza A, Influenza B, Influenza C, Isavirus and Thiogotovirus. Another genus includes the Quaranfil, Johnston Atoll and Lake Chad viruses which are associated with mild to severe arboviral infections (Presti et al, *J. Virol.* 83(22):11599-11606, 2009). Influenza viruses have caused significant mortality and morbidity. Influenza A, for example, has been responsible for all flu pandemics and has resulted in millions of deaths world wide. Examples include the Asiatic (Russian) flu of 1889-1890 which killed an estimated 1 million people, the Spanish flu of 1918-1920 which killed approximately 40 million people and the Asian and Hong Kong flu outbreaks between 1957 and 1969 which killed an estimated 2 million people.

Swine influenza (also referred to as pig influenza, swine flu, hog flu and pig flu) is an infection by any one of several types of swine influenza virus. A swine influenza virus is any strain of influenza virus which is endemic in pigs (Bouvier and Palese, *Vaccine* 26 Suppl. 4:D49-53, 2008). Known swine flu viruses include Influenza A sub-types $H_1N_1$, $H_1N_2$, $H_3N_2$, $H_3N_1$, $H_3N_2$ and $H_2N_3$. There are also sub-types of Influenza C virus (Heinen, *Veterinary Science Journal*, 15 Sep. 2009).

Swine influenza virus is endemic in pigs. The transmission of an endemic pig strain of influenza virus to humans is referred to as zoonotic swine flu and can cause influenza-like illnesses such as chills, fever, sore throat, muscle pain, severe headache, coughing and general discomfort. Much of this discomfort and symptoms is caused by the body's response to the infection. Both innate and acquired immune responses can lead to production of large amounts of cytokines and growth factors resulting in migration of immune cells such as lymphocytes and macrophages to various locations and release of other molecules such as histamines. This can result in fluid accumulation such as in the lungs leading to significant respiratory complications.

Avian influenza (also referred to as avian flu and bird flu) refers to zoonotic avian flu which is adapted to humans (Harder and Ortrud, *Influenza Report*, Chapter 2, 2006). All known avian influenza viruses are Influenza A viruses. One particularly significant sub-type is referred to as Influenza A sub-type $H_5N_1$ other sub-types include $H_5N_7$, $H_7N_3$, $H_7N_7$ and $H_9N_2$(Leong et al, *Ann Acad Med Sngap* 37(6):504-509, 2008). Since the outbreak of $H_5N_1$ in 1987, millions of poultry have been killed throughout Europe, Asia and Africa. Hundreds of human lives have also been lost.

The influenza viruses and other Orthomyxoviridae have been and continue to be significant pathogens in humans and animals including high density farming animals such as pigs and poultry. There is a need to identify agents which can reduce infection and spread of these viruses and/or which ameliorate conditions caused thereby.

SUMMARY

The present disclosure teaches a sulfated polysaccharide and in an embodiment, a fraction of sulfated polysaccharides, having an average molecular weight of 4,000 Daltons or greater which inhibit a virus of the Orthomyxoviridae family. The sulfated polysaccharide may be a purified compound or part of a formulation, extract or a physically, chemically and/or enzymatically derivatized polysaccharide preparation or fraction. Examples of Orthomyxoviridae include influenza viruses such as a member or sub-type of Influenza A, B or C or a variant thereof. Reference to "Influenza A" includes the sub-type $H_xN_y$, where x is types 1 to 16 inclusive and y is types 1 to 9 inclusive. Examples include swine influenza and avian influenza such as swine influenza $H_1N_1$, $H_1N_2$, $H_3N_1$, $H_3N_2$ and $H_2N_3$ and avian influenza $H_5H_1$, $H_5N_7$, $H_7N_3$, $H_7N_7$ and $H_9N_2$.

Accordingly, a method is provided for the treatment or prophylaxis of Orthomyxoviridae infection in a subject or a condition or symptom associated with orthomyxoviral infection, the method comprising contacting the virus or cells infected by the virus with an effective amount of a sulfated polysaccharide having an average molecular weight of 4,000 Daltons or greater.

Another aspect taught herein is a method for controlling spread of an Orthomyxoviridae virus, the method comprising contacting the virus or a surface upon which a virus may be exposed with an effective amount of a sulfated polysaccharide having an average molecular weight of 4,000 Daltons or greater.

The present disclosure further contemplates the use of a sulfated polysaccharide having an average molecular weight of 4,000 Daltons or greater in the manufacture of a medicament or preventative which inhibits spread of an Orthomyxoviridae virus. A "preventative" in this context includes a health supplement or functional food for general use such as in the form of consumer goods or consumer foods. A "medicament" includes an agent suitable for clinical use. Reference to "treatment or prophylaxis" includes ameliorating conditions or symptoms associated with infection such as over-stimulation of cytokine and growth factor production. This can lead to lung or organ damage and can exacerbate symptoms of infection.

A composition for use in the treatment, prophylaxis and control of an Orthomyxoviridae virus infection is also provided, the composition comprising a sulfated polysaccharide having an average molecular weight of 4,000 Daltons or greater. In an embodiment, the composition is in the form of a hand lotion, soap, hand cream, gel, detergent, spray, aerosol or powder. In another embodiment, the composition is in the form of a skin, surface or nasal spray. In still another embodiment, the composition is of a pharmaceutical grade for clinical application. In still another embodiment, the composition is a functional food or food supplement or as other forms of consumer goods.

The method and compositions taught herein are also proposed to be used alone or in combination with other anti-viral therapies or protocols or reagents used to control viral spread. For example, face masks and gloves impregnated with the sulfated polysaccharide are contemplated. Examples of anti-viral agents which can be used in combination with the sulfated polysaccharides include oseltamivir (tamiflu), zanamivir (relenza), amantadine, rimantidine and an interferon.

A method is also provided hereinfor reducing flu-like symptoms associated with infection by an influenza virus, the method comprising administering to a subject an effective amount of a sulfated polysaccharide having an average molecular weight of 4,000 Daltons or greater.

Such flu-like symptoms include conditions associated with excess cytokine and growth factor production.

Reference to a "sulfated polysaccharide" includes a fucose-rich and rhamnose-containing sulfated polysaccharide and a galactofucan polysaccharide. Generically, the sulfated polysaccharides may also be referred to as fucoidans. The present invention contemplates a range of sources of sulfated polysaccharides such as fucose-rich and rhamnose-containing sulfated polysaccharides. Sources include fresh, frozen or dried preparations or extracts of brown seaweed or green seaweed as well as echinoderms including sea urchins and sea cucumbers (see Berteau and Mulloy, *Glycobiology* 13(6):29-40, 2003). As indicated above, the sulfated polysaccharide may be a purified compound or part of a formulation, extract or a physically, chemically and/or enzymatically derivatized polysaccharide preparation.

By "4,000 Daltons or greater" includes from about 4,000 Daltons to about 5 million Daltons.

DETAILED DESCRIPTION

Throughout this specification, unless the context requires otherwise, the word "comprise", or variations such as "comprises" or "comprising", will be understood to imply the inclusion of a stated element or integer or step or group of elements or integers or steps but not the exclusion of any other element or integer or step or group of elements or integers or steps.

As used in the subject specification, the singular forms "a", "an" and "the" include plural aspects unless the context clearly dictates otherwise. Thus, for example, reference to "a virus" includes a single virus, as well as two or more viruses; reference to "a sulfated polysaccharide" includes a single type of polysaccharide or two or more different types; reference to "an extract" includes a single extract, as well as two or more extracts; reference to "the disclosure" includes single and multiple aspects taught by the disclosure; and so forth.

The present disclosure teaches a formulation comprising a sulfated polysaccharide or a fraction of sulfated polysaccharides or a purified form of a sulfated polysaccharide having an average molecular weight of 4,000 Daltons or greater and in a concentration of from about 1% w/w with other excipients or components to 100% pure for use in inhibiting a virus from the Orthomyxoviridae family and to ameliorate conditions associated with virus infection. Hence, the present disclosure enables a purified compound suitable for use as a pharmaceutical medicament as well as extracts or compositions suitable as health supplements or functional or medical foods or food additives for more general application such as in the form of consumer goods. Reference to "inhibiting" a virus includes inhibiting viral entry or penetration into a cell, viral replication, assembly and/or release. Particular forms of inhibition target viral entry and replication. The present disclosure is also directed to controlling conditions associated with orthovirus infection such as over-stimulation of innate and acquired immune responses leading to over production of cytokines and growth factors which can damage the lung or other organs and can lead to exacerbated symptoms of infection.

Accordingly, a method is provided for inhibiting a virus of the Orthomyxoviridae family or a condition associated with viral infection, the method comprising contacting the virus or a cell infected with the virus with an effective amount of a formulation comprising a sulfated polysaccharide having an average molecular weight of 4,000 Daltons or greater. The term "viral infection" in this context means "orthomyxoviral infection". The term "orthomyxo" is used to describe a member of the Orthomyxoviridae family.

Another aspect taught herein is a method for controlling spread of an Orthomyxoviridae virus, the method comprising contacting the virus or a surface upon which a virus may be exposed with an effective amount of a sulfated polysaccharide having an average molecular weight of 4,000 Daltons or greater.

The sulfated polysaccharide is generally from 4,000 Daltons to approximately 5 million Daltons including approximately 5,000, 10,000, 15,000, 20,000, 30,000, 50,000, 70,000, 90,000, 100,000, 300,000, 500,000, 700,000, 900,000, 1 million, 2 million, 3 million, 4 million and 5 million Daltons or an average molecular weight in between these particular sizes.

In an embodiment, the formulation comprises from about 1% w/w sulfated polysaccharide to 100% purity including 1, 5, 10, 20, 30, 40, 50, 60, 70, 80, 90 and 100% w/w purity or a purity in between these values. A "pure" compound is regarded herein as a formulation. Hence, terms such as extract, compound, medicament, preventive, agent, pharmaceutical, sulfated polysaccharide and the like all refer to a formulation comprising from 1% w/v to 100% w/v polysaccharide. The sulfated polysaccharide may, therefore, be a purified compound, part of a formulation or extract or may be in the form of a physically, chemically and/or enzymatically derivatized polysaccharide preparation. A formulation may also comprise the sulfated polysaccharide together with polyphloroglucinol and/or polyphenol and/or another anti-viral agent. Examples of other anti-viral agents formulated together or separately to the sulfated polysaccharide include oseltamivir (tamiflu), zanamivir (relenza), amantadine and rimantidine as well as cytokines such as an interferon (e.g. IFNα and IFNγ). Furthermore, the sulfated polysaccharide may be a single chemical species or entity or may be a mixture of two or more different types of sulfated polysaccharide. The extracts or compounds may be subject to depyrogenation to remove any toxins or toxicants, if required.

In another embodiment, the formulation is or comprises a fraction of sulfated polysaccharides, the fraction defined by average molecular weight, degree of sulfation, degree of carboxylation, ionic charge and/or anti-viral activity. For example, a large sulfated polysaccharide may be subjected to physical disruption, chemical derivatization and/or enzymatic digestion and fractions collected based on any one or more of the above-listed parameters. A fraction having the desired anti-viral activity is then collected and optionally subjected to further purification. Such a "fraction" is encompassed by the terms "formulation", "extract", "compound", "medicament", "preventative", "agent", "pharmaceutical" and "sulfated polysaccharide".

The sulfated polysaccharide may be derived from any convenient source and includes forms such as fucan sulfate, fucose sulfate, a galactofucan, a fucose-rich sulfated polysaccharide, a rhamnose-containing sulfated polysaccharide, chondroitin sulfate, fucoidan, heparin sulfate and a glycosaminoglycan as well as modified forms thereof. All these forms are encompassed by the term "sulfated polysaccharide". A "modified" form includes an enzymatically-, physically- or chemically-generated fraction. It also includes cation-modified sulfated polysaccharides, wherein other metal cations, including monovalent, divalent and multivalent cations make up a counterion component. In one embodiment, the sulfated polysaccharide is isolated from a brown seaweed of the Class Phaeophyceae, Order Laminariales (e.g. Akkesiphycacease, Alariaceae, Chordaceae, Costariaceae, Laminariaceae, Lessoniaceae and Pseudochordaceae) or Order Fucales (e.g. Bifurcariopsdaceae, Durvillaeaceae, Fucaceae, Himanthallaceae, Hormosiraceae, Notheiaceae, Sargassaceae and Seirococcaceae). Examples of Order Laminariales seaweed includes species of the Genus *Undaria* such as but not limited to *Undaria pinnatifida*, or related species such as *Alaria esculenta*, *Saccorhiza polysaccharides*, *Undaria undarioides*, *Undaria peterseniana* and *Laminaria* sp such as *Laminaria digitata*, *Laminaria hyperborean*, *Laminaria ochroleuca*, *Laminaria saccharina*, *Laminaria agardhii*, *Laminaria angustata*, *Laminaria bongardina*, *Laminaria cuneifolia*, *Laminaria dentigera*, *Laminaria ephemera*, *Laminaria farlowii*, *Laminaria groenlandica*, *Laminaria japonica*, *Laminaria longicruris*, *Laminaria nigripes*, *Laminaria ontermedia*, *Laminaria pallida*, *Laminaria platymeris*, *Laminaria saccharina*, *Laminaria setchellii*, *Laminaria sinclairli*, *Laminaria solidungula* and *Laminaria stenophylla*. Examples of the Order Fucales seaweed include species of the Genus *Fucus* such as but not limited to *Fucus vesiculosus*, *Fucus ceranoides*, *Fucus chalonii*, *Fucus cottonii*, *Fucus distichus*, *Fucus evanescens*, *Fucus gardneri*, *Fucus nereideus*, *Fucus serratus*, *Fucus spermophorus*, *Fucus spiralis*, *Fucus tendo* and *Fucus virsoides*.

Other orders of brown seaweed include Ascoseirales, Cutleriales, Desmarestiales, Dictyotales, Discosporangiales, Extocarpales, Ishigeales, Nemodermatales, Onslowiales, Ralfsiales, Scytosiphonales, Scytothaminales, Sphacelariales, Sporochnales, Syringodermatales, Tilopteridales and Incertaesedis.

Particular brown seaweeds include species of *Ascoseira, Cutleria, Microzonia, Zanardinia, Arthrocladia, Desmarestia, Himantothallus, Phaeurusm, Dictyopteris, Dictyota, Dilophus, Distromium, Glossophora, Homoeostrichus, Lobophora, Lobospira, Newhousia, Pachydictyon, Padina, Spatoglossum, Stypopodium, Taonia, Zonaria, Scoresbyella, Choristocarpus, Discosporangium, Acinetospora, Feldmannia, Geminocarpus, Hincksia, Pogotrichum, Pylaiella, Adenocystis, Caepidium, Utriculidium, Acrothrix, Ascoseirophila, Asperococcus, Austrofilum, Chordaria, Cladosiphon, Corycus, Delamarea, Dictyosiphon, Elachista, Eudesme, Giraudia, Gononema, Halothrix, Haplogia, Hecatonema, Heterosaundersella, Hummia, Isthmoplea, Laminariocolax, Laminarionema, Leathesia, Leptonematella, Litosiphon, Microspongium, Mikrosyphar, Myelophycus, Myriogloea, Myrionema, Myriotrichia, Papenfussiella, Petrospongium, Pleurocladia, Polytretus, Proselachista, Protectocarpus, Punctaria, Sauvageaugloia, Soranthera, Sorocarpus, Spermatochnus, Sphaerotrichia, Stictyosiphon, Streblonema, Striaria, Stschapovia, Tinocladia, Chordariopsis, Asterocladon, Ectocarpus, Kuckuckia, Mesospora, Asterotrichia, Bachelotia, Bifurcariopsis, Durvillaea, Ascophyllum, Fucus, Hesperophycus, Pelvetia, Pelvetiopsis, Silvetia, Xiphosphora, Himanthalia, Hormosira, Notheia, Anthophycus, Axillariella, Bifurcaria, Bifurcariopsis, Carpoglossum, Caulocystis, Coccophora, Cystophora, Cystoseira, Halidrys, Hizikia, Hormophysa, Myagropsis, Myogropsis, Myriodesma, Sargassum, Turbinaria, Cystophaera, Marginariella, Phyllospora, Seirococcus, Ishige, Akkesiphycus, Alaria, Aureophycus, Druehlia, Eualaria, Hirome, Lessoniopsis, Pleurophycus, Pterygophora, Undaria, Undariella, Undariopsis, Chorda, Agarum, Costaria, Dictyoneurum, Thalassiophyllum, Arthrothamnus, Costularia, Cymathere, Feditia, Gigantea, Laminaria, Macrocystis, Nereocystis, Pelagophycus, Pelagophycus, Macrocystis, Phycocastanum, Phyllariella, Polyschidea, Postelsia, Pseudolessonia, Saccharina, Streptophyllopsis, Ecklonia, Eckloniopsis, Egregia, Eisenia, Lessonia, Pseudochorda, Nemoderma, Onslowia, Verosphacella, Neoralfsia, Basispora, Hapalospongidion, Jonssonia, Lithoderma, Myrionemopsis, Petroderma, Porterinema, Pseudolithoderma, Ralfsia, Chnoospora, Colpomenia, Hydroclathrus, Petalonia, Rosenvingea, Scytosiphon, Bodanella, Coelocladia, Heribaudiella, Phaeostroma, Asteronema, Scytothamnus, Stereocladon, Splachnidium, Cladostephus, Sphacelaria, Sphacella, Alethocladus, Halopteris, Stypocaulon, Austronereia, Bellotia, Carpomitra, Encyothalia, Nereia, Perisporochnus, Perithalia, Sporochnema, Sporochnus, Tomaculopsis, Syringoderma, Halosiphon, Masonophycus, Phyllariopsis, Saccorhiza, Stschapovia, Haplospora, Phaeosiphoniella, Tilopteris, Neolepioneuma, Analipus* and *Phaeostrophion*.

Particular brown seaweeds include species of *Adenocystis, Alaria, Ascophyllum, Chorda, Cladosiphon, Desmarestis, Dictyota, Duvillea, Ecklonia, Ectocarpus, Egregia, Fucus, Halidrys, Himanthalia, Hormosiria, Lethesia, Lessonia, Macrocystis, Nereocystis, Padina, Pelagophycus, Pelvatia, Pilaiella, Postelsia, Saccrhiza, Sargassum, Sphacelaria* and *Turbinaria*.

Other sources include green seaweed and echinoderms such as sea urchins and sea cucumbers (see Berteau and Mulloy, 2003, supra). Examples of green seaweed include *Ulva* sp, *Enteromorpha* sp, *Codium* sp, *Caulerpa* sp and *Halimala* sp.

In an embodiment, the sulfated polysaccharide is sourced from *Undaria pinnatifida* or *Fucus vesiculosus*.

Hence, the sulfated polysaccharide may be from any brown or green seaweed as well as echinoderms.

An example of a sulfated polysaccharide is a galactofucan sulfate. The isolation of a average galactofucan sulfate from *Undaria pinnatifida* is described in U.S. Pat. No. 7,056,620, the contents of which are incorporated herein by reference.

This description applies to other sulfated polysaccharides from a variety of brown and green seaweeds. Galactofucan sulfate found in *Undaria* is a complex heterogeneous carbohydrate whose component sugars are primarily galactose and fucose and small amounts of other sugars. The average molecular weight may range from about 30,000 to about 1,200,000, typically between about 500,000 to about 1,200,000. Galactofucan sulfate, and other complex naturally occurring sulfated polysaccharides, are highly complex molecules. The structure of galactofucan sulfate comprises small sections of the molecule which are random, alternating or block copolymers of galactose and fucose. Linkage between the sugar units may vary but is predominantly by 1-3 linkages. The sulfur content is typically between about 4.5-6.5% which indicates a sulfate content of about 18% as $SO_3Na$. Hence, galactofucan sulfate has an average of about one sulfate group for every two sugar residues. Other sulfated polysaccharides are fucose-rich sulfated polysaccharides.

The sulfated polysaccharide for use in the method and composition taught herein may be sourced from the whole plant or any part of the plant, such as the leaves, stem, spores, or a combination thereof. The starting material may be fresh, frozen or dried material.

The brown or green seaweed extract may be obtained by any suitable method to extract plant material that enables at least partial separation of the sulfated polysaccharide from other plant material. For example, an acid/water mixture is used to extract the seaweed. Conveniently, the acid is sulfuric acid. Suitably, the acid/water extract is then neutralized, typically with an alkali metal hydroxide, and filtered or dialyzed to remove unwanted components including pyrogens, if necessary. After filtration or dialysis, the extract may be used as a liquid or dried by any method such as freeze drying or oven drying or spray drying. Typically, such an extract includes from at least about 1% w/v sulfated polysaccharide to about 100% w/v.

An example of an extraction procedure utilizes an acid/water mixture at a pH of between about 0 to about 2, such as between about 0 and 1, at temperatures between about 0 and 30° C., such as between about 15 and about 25° C. The present disclosure enables any of a range of extraction procedures.

Typically, a sulfated polysaccharide extracted by the above method has an average molecular weight of 4,000 Daltons or greater, particularly 5,000 Daltons or greater, particularly 8,000-9,000 Daltons or greater, particularly 20,000 Daltons or greater, particularly about 100,000 or greater, particularly 200,000 Daltons or greater and even more particularly 500,000 Daltons or greater. Typically, the average molecular weight for the upper 10% material is about 5 million Daltons. Hence, a range of from about 4,000 Daltons to about 5 million Daltons is contemplated herein. In an embodiment, the sulfated polysaccharide is a hydrolyzed *Fucus* fucoidan with an average molecular weight of approximately 8,000-9,000 Daltons.

An example of a composition comprises extracts from *Undaria* sporophyll and fucus material. However, the present disclosure teaches any source of sulfated polysaccharide such as from brown or green seaweed and from echinoderms. Furthermore, reference to "sulfated polysaccharide" includes fucan sulfate, fucose-rich sulfated polysaccharides, a rhamnose-containing sulfated polysaccharide, a galactofucan and the like. The term "fucoidan" may also be used to describe the sulfated polysaccharides from brown seaweeds, as well as physically, chemically and/or enzymatically derivatized forms thereof.

The sulfated polysaccharides may also be extracted by procedures such as maceration, decoction, extraction under reflux, extraction with aid of ultrasonics, extraction aided by partitioning between solvent phases and supercritical extraction with or without co-solvents.

The effective amount of the sulfated polysaccharide for use in the method or composition of the present disclosure is dependent on the dosage protocol, the intended recipient, the virus and whether the virus is in a latent or active stage. Dosage levels contemplated herein include between about 0.001 g to about 20 g per day, suitably between about 0.01 g and 10 g and suitably between about 0.5 g and about 1 g of sulfated polysaccharide or amounts in between. It is to be understood that a person skilled in the art would be able to determine sufficient dosage levels of sulfated polysaccharide to administer to a person (or animal) to obtain effective antiviral activity.

Hence, the present disclosure teaches a method for inhibiting a virus of the Orthomyxoviridae family of viruses or to ameliorate a condition associated with viral infection, the method comprising contacting the virus or a cell infected with the virus with an amount of a formulation comprising a sulfated polysaccharide in a form selected from the list consisting of:

(i) a preparation comprising at least 1% w/w sulfated polysaccharide;
(ii) a preparation comprising at least 10% w/w sulfated polysaccharide;
(iii) a preparation comprising at least 50% w/w sulfated polysaccharide;
(iv) a preparation comprising at least 80% w/w sulfated polysaccharide;
(v) a preparation comprising at least 90% w/w sulfated polysaccharide;
(vi) a substantially pure form of the sulfated polysaccharide;
(vii) a fraction of sulfated polysaccharide;
(viii) a chemically derivatized form of sulfated polysaccharide; and
(ix) a sulfated polysaccharide admixed with another medicament or excipient such as an anti-viral agent or polyphloroglucinol or polyphenol;

wherein the sulfated polysaccharide comprises an average molecular weight of from about 4,000 Daltons to 5 million Daltons. In an embodiment, the sulfated polysaccharide is a fucose-rich sulfated polysaccharide or a rhamnose-containing sulfated polysaccharide. The present disclosure teaches any fucoidan.

As indicated above, a "chemically derivatized" form includes a cation modified sulfated polysaccharide, wherein other metal cations, including monovalent, divalent and multivalent cations make up the counterion component of the polysaccharide. "Enzymatically derivatized" includes hydrolyzed.

The virus of the Orthomyxoviridae family may be any genus of the six currently identified within the family, i.e. a virus of the genus Influenza A, Influenza B, Influenza C, Isavirus, Thogotovirus and/or a Quarandfil/Johnston Atoll/Lake Chad genus of virus or variants thereof. In an embodiment, the virus is an influenza virus of the Influenza A, Influenza B and/or Influenza C genera or sub-types thereof or variant forms thereof. A "variant form" of virus includes viruses having genomic elements derived from two or more sub-types of Influenza A, Influenza B and/or Influenza C or a sub-type thereof. Insofar as the virus is an Influenza A or comprises genomic elements of Influenza A, it may be any sub-type defined herein as $H_xN_y$ wherein H is hemagglutin type$_x$ wherein$_x$ is 1 to 16 inclusive and N is neuraminidase of type$_y$ when$_y$ is 1 to 9 inclusive. Reference to any of Influenza A, B or C includes variants and sub-types. A virus of the Orthomyxoviridae family is encompassed by the term "orthomyxovirus".

Reference to "1 to 16" includes types 1, 2, 3, 4, 5, 6, 7, 8, 9, 10, 11, 12, 13, 14, 15 and 16. Reference to "1 to 9" includes types 1, 2, 3, 4, 5, 6, 7, 8 and 9. Particular Influenza A sub-types associated with swine flu include $H_1N_1$, $H_1N_2$, $H_3N_1$, $H_3N_2$ and $H_2N_3$. Examples of Influenza A sub-types associated with bird flu include $H_5N_1$, $H_5H_7$, $H_7N_3$, $H_7H_7$ and $H_9N_2$.

The virus may also be a mixture of different genera of Orthomyxoviridae or a mixture of different sub-types of a genus of Orthomyxoviridae viruses or may be a variant or a particular virus.

Accordingly, another aspect taught herein is a method for inhibiting a virus of the Orthomyxoviridae family of viruses or of ameliorating symptoms associated with viral infection, the method comprising contacting the virus or cell infected with the virus with a sulfated polysaccharide having an average molecular weight of 4,000 Daltons or greater wherein the virus is an Influenza A, Influenza B and/or Influenza C virus or a variant thereof wherein the Influenza A virus or its variant is defined by $H_xN_y$ wherein $H_x$ is a hemagglutin wherein x, is from 1 to 16 and $N_y$ is neuraminidase wherein$_y$ is from 1 to 9.

In a related embodiment, the present disclosure enables a method for inhibiting a virus of the Orthomyxoviridae family of viruses or ameliorating symptoms associated with viral infection, the method comprising contacting the virus or a cell infected with the virus with an amount of a formulation comprising a sulfated polysaccharide in a form selected from the list consisting of:
(i) a preparation comprising at least 1% w/w sulfated polysaccharide;
(ii) a preparation comprising at least 10% w/w sulfated polysaccharide;
(iii) a preparation comprising at least 50% w/w sulfated polysaccharide;
(iv) a preparation comprising at least 80% w/w sulfated polysaccharide;
(v) a preparation comprising at least 90% w/w sulfated polysaccharide;
(vi) a substantially pure form of the sulfated polysaccharide;
(vii) a fraction of sulfated polysaccharide;
(viii) a chemically derivatized form of sulfated polysaccharide; and
(ix) a sulfated polysaccharide admixed with another medicament or excipient such as an anti-viral agent or polyphloroglucinol or polyphenol;
wherein the sulfated polysaccharide comprises an average molecular weight of from about 4,000 Daltons to 5 million Daltons, wherein the virus is an Influenza A, Influenza B and/or Influenza C virus or a variant thereof and wherein the Influenza A virus or its variant is defined by $H_xN_y$ wherein $H_x$ is a hemagglutin wherein$_x$ is from 1 to 16 and $N_y$ is neuraminidase wherein$_y$ is from 1 to 9.

Of relevance to human and animal health and well being is the control of flu and flu-like viruses such as human flu, swine flu and avian flu viruses, which are generally of an Influenza A virus or variant thereof. There are also some forms of Influenza C associated with infection in pigs. "Animals" contemplated herein include grazing and lot animals as well as pet animals. Where appropriate, wild animals may also be treated.

Hence, in one embodiment, a method is provided for inhibiting swine flu virus or ameliorating symptoms of viral infection, the method comprising contacting the virus or cell infected with the virus with a sulfated polysaccharide having an average molecular weight of from 4,000 Daltons to 5 million Daltons.

Also provided is a method for inhibiting an avian flu virus or ameliorating symptoms of viral infection, the method comprising contacting the virus or cell infected with the virus with a sulfated polysaccharide having an average molecular weight of from 4,000 Daltons to 5 million Daltons.

The present disclosure further teaches a method for inhibiting an $H_1N_1$ virus or $H_5N_1$ virus or ameliorating symptoms of viral infection, the method comprising contacting the virus or cell infected with the virus with a sulfated polysaccharide having an average molecular weight of from 4,000 Daltons to 5 million Daltons.

The present disclosure also contemplates a method for inhibiting a virus selected from:
(1) an Influenza A virus of subtype:
  (a) $H_xN_y$ I wherein $H_x$ is hemagglutin and$_x$ is from 1 to 16 and $N_y$ is neuraminidase and$_y$ is from 1 to 9;
  (b) $H_1N_1$;
  (c) $H_1N_2$;
  (d) $H_3N_1$;
  (e) $H_3N_2$;
  (f) $H_2N_3$;
  (g) $H_5N_1$;
  (h) $H_5N_7$;
  (i) $H_7N_3$;
  (j) $H_7N_7$; and/or
  (k) $H_9N_2$;
(2) an Influenza B virus;
(3) an Influenza C virus; and
(4) a variant of a virus listed above; the method comprising contacting the virus or a cell infected with the virus with an amount of a formulation comprising a sulfated polysaccharide in a form selected from:
(i) a preparation comprising at least 1% w/w sulfated polysaccharide;
(ii) a preparation comprising at least 10% w/w sulfated polysaccharide;
(iii) a preparation comprising at least 50% w/w sulfated polysaccharide;
(iv) a preparation comprising at least 80% w/w sulfated polysaccharide;
(v) a preparation comprising at least 90% w/w sulfated polysaccharide;
(vi) a substantially pure form of the sulfated polysaccharide;
(vii) a fraction of sulfated polysaccharide;
(viii) a chemically derivatized form of sulfated polysaccharide; and
(ix) a sulfated polysaccharide admixed with another medicament or excipient such as an anti-viral agent or polyphloroglucinol or polyphenol;
wherein the sulfated polysaccharide comprises an average molecular weight of from about 4,000 Daltons to 5 million Daltons.

By "inhibiting" in relation to a virus, includes inhibiting or retarding infection, attachment, penetration, replication, assembly or release of the virus. In an embodiment, the inhibition at the level of cell penetration or attachment and/or replication.

Furthermore, the sulfated polysaccharides herein are proposed to ameliorate symptoms or conditions of viral infection such as over-stimulation of cytokine and growth factor production which can damage the lung and other organs. This can occur, for example, by an over-stimulated innate or acquired immune system. The cytokines and growth factors can also lead to exacerbated symptoms of infections such as flu-like symptoms.

The formulations of the present invention may be in a form of a pharmaceutical-grade composition or purified medicament, a health food supplement or a preventative such as a hand wash, nasal wash, skin lotion, surface disinfectant, spray, aerosol, gel, solution, powder or cream. The formulations include a purified compound or an extract or fraction or an enriched preparation. The compounds or formulations may also be regarded as consumer goods, consumer foods or consumer supplements.

The sulfated polysaccharide or extract comprising same may be administered with a pharmaceutical carrier, which is non-toxic to cells and the subject.

The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The formulations taught herein for oral administration are generally presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the sulfated polysaccharide with the carrier which constitutes one or more ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In an embodiment, the sulfated polysaccharide is formulated with polyphloroglucinol and/or polyphenol.

The sulfated polysaccharides of the present invention may be administered orally, parenterally (including subcutaneous injections, intraperitoneal, intravenous, intramuscular, intrasternal injection or infusion techniques), by inhalation spray, or rectally, in dosage unit formulations containing conventional non-toxic pharmaceutically acceptable carriers, adjuvants and vehicles.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The sulfated polysaccharides may also be used in a surface, disinfectant, hand wash, skin wash, lotion, cream or used as a health supplement or functional food or medicine or consumer goods.

The effective dosage of the sulfated polysaccharides in therapy may vary depending on the particular compound employed, the mode of administration, the condition being treated and the severity of the condition being treated. Thus, the dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Some sulfated polysaccharides such as fucose-rich sulfated polysaccharides and/or fucoidans are considered to be a soluble fibre and are not broken down by mammalian enzymes. However, there is some serum uptake of the material after oral ingestion. It is estimated at >10 g/ml on an intake of 3 g of a 75% pure polysaccharide per day, and reached 4 µg/ml on an intake of 3 g of '10%' polysaccharide.

Uptake of sulfated polysaccharide can be measured in any number of ways such as by antibody assays (see Irhimeh et al, *Methods Fnd Exp. Clin. Pharmacol.* 27(10):705-710, 2005), dye-based methods including alcian blue (Scott and Darling, *Histochemic* 5:221-233, 1965), dimethyl blue DMMB (deZong et al, *Clinical Chemistry* 35(7):1472-1477, 1981) and direct chemical methods such as the Dubois method.

The present disclosure enables sulfated polysaccharide formulations for medical or clinical use or for the health food industry as health supplements or functional foods or medicines. The formulations may also be used for veterinary or agricultural applications such as in animal husbandry or in animal maintenance such as for closely quartered pigs, cattle and poultry as well as grazing, farm, pet and wild animals. The formulations have, therefore, a wide spectrum of use in humans and all mammals.

Hence, although the formulations comprising the sulfated polysaccharides are useful for controlling spread of influenza in humans, the formulations may also be used in non-human animals such as pigs, cattle, horses, sheep, donkeys, camels and poultry such as chickens, bantams, ducks, turkeys and geese. The present disclosure further teaches functional pet foods for dogs and cats and as general agricultural and aquaculture food additives.

Another aspect contemplated herein is the use of an extract of a brown seaweed, green seaweed and/or echinoderm comprising a sulfated polysaccharide or fraction of sulfated polysaccharides in the manufacture of a medicament or health supplement to control infection and spread of a flu virus.

The sulfated polysaccharides may also be considered a functional food additive or extract for use in controlling infection and spread of flu virus.

Reference to "flu virus" in this context includes, in an embodiment, swine flu and avian flu in humans, pigs and/or poultry.

Yet another aspect of the contemplated herein is a method for reducing flu-like symptoms associated with infection by an influenza virus, the method comprising administering to a subject an effective amount of a sulfated polysaccharide having an average molecular weight of 4,000 Daltons or greater. This includes molecular weights of from about 4,000 Daltons to about 5 million Daltons.

The sulfated polysaccharide is as defined above. The flu-like symptoms include conditions induced by an over production of cytokines and growth factors.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The present disclosure illustratively described herein suitably may be practiced in the absence of any element or elements, limitation or limitations which is not specifically disclosed herein.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

When a range is recited herein, it is intended that all subranges within the stated range, and all integer values within the stated range, are intended, as if each subrange and integer value was recited.

Aspects are further described by the following non-limiting Examples.

Example 1

Formulations

Table 1 provides a summary of the sulfated polysaccharide formulations tested against orthomyxovirus.

TABLE 1

| Sulfated polysaccharide formulation | |
|---|---|
| ID No. | Source |
| 09-001329 | *Undaria pinnatifida* |
| 09-001330 | *Fucus vesiculosis* |

TABLE 1-continued

| Sulfated polysaccharide formulation | |
|---|---|
| ID No. | Source |
| 09-001331 | *Fucus vesiculosis* |
| 09-001332 | *Fucus vesiculosis* |
| 09-001333 | *Undaria pinnatifida* |
| 09-001334 | *Undaria pinnitafida* |

The particular characteristics of 09-001334 and 09-001329 are present in Table 2.

TABLE 2

| Characteristics of two sulfated polysaccharides | | |
|---|---|---|
|  | 09-001334 | 09-001329 |
| Total Carbohydrates (%) | 43.5 | 53.0 |
| Fucose (%) | 23.9 | 30.7 |
| Galactose (%) | 18.4 | 22.3 |
| Uronic Acids (%) | 6.6 | — |
| Fucoidan (%) | 91.4 | 96 |
| $H_2O$ (%) | 8.3 | 3.7 |
| Acetyl (%) | 2.5 | 0.2 |
| Sulfate (%) | 25.2 | 0.2 |
| Ca (%) | 1.3 | 0.7 |
| Na (%) | 4.9 | 6.2 |
| K (%) | 2.5 | — |
| Mg (%) | 0.8 | — |
| Peak MW (kDa) | 569.6 | 119.9 |
| MW % >600 kDa | 22.4 | 17.1 |
| MW % 1100-1600 kDa | 6.3 | 2.5 |
| MW % 200-1100 kDa | 32.3 | 22.8 |
| MW % 60-200 kDa | 18.6 | 24.2 |
| MW % 20-60 kDa | 8.4 | 15.5 |
| MW % 5-20 kDa | 2.2 | 6.8 |
| MW % <5 kDa | 9.8 | 11.1 |
| pH | 5.89 | 6.9 |

Percentages are as % (w/w) relative to the dried mass.
kDa, kilo Daltons.
MW, average molecule weight.

Example 2

Anti-Viral Activity

The sulfated polysaccharides are tested for anti-orthomyxoviral activity using the National Institute of Allergy and Infections Diseases (NIAID), Division of Microbiology and Infectious Diseases (DMID), Antiviral Evaluation Program. Information can be found on its website (http://niaid-aacf.org/index.html).

NIAID provides a panel of influenza viruses including Influenza A/California/07/2009 ($H_1N_1$); Influenza A/Brisbane/10/2007 ($H_3N_2$); Influenza A/Vietnam/1203/2004H ($H_5N_1$); and Influenza B/Florida/4/2006.

The cytopathic effect (CPE) of the viruses infecting cells with and without sulfated polysaccharides to be tested is then determined. CPE is determined by light microscopy and a neutral red assay. The results are shown in Table 3.

TABLE 3

| Effects of sulfated polysaccharides on viral strains | | | | | | | | | | | |
|---|---|---|---|---|---|---|---|---|---|---|---|
| ARB # | Assay | Vehicle | Virus | Strain | Cell Line | Drug Unit | Trial | EC50 | EC90 | IC50 | SI |
| 09-001329 | Neutral Red | H2O | Flu A (H1N1) | California/07/ 2009 | MDCK | µg/ml | 1 | 0.64 |  | >100 | >160 |
| 09-001329 | Visual | H2O | Flu A (H1N1) | California/07/ 2009 | MDCK | µg/ml | 1 | 0.35 |  | >100 | >290 |

TABLE 3-continued

Effects of sulfated polysaccharides on viral strains

| ARB # | Assay | Vehicle | Virus | Strain | Cell Line | Drug Unit | Trial | EC50 | EC90 | IC50 | SI |
|---|---|---|---|---|---|---|---|---|---|---|---|
| 09-001329 | Neutral Red | H2O | Flu A (H1N1) | California/07/ 2009 | MDCK | µg/ml | 2 | 0.6 | | >100 | >170 |
| 09-001329 | Visual | H2O | Flu A (H1N1) | California/07/ 2009 | MDCK | µg/ml | 2 | 0.07 | | >100 | >1400 |
| 09-001329 | Virus Yield | H2O | Flu A (H1N1) | California/07/ 2009 | MDCK | µg/ml | 3 | | 26 | | >3.8 |
| 09-001329 | Visual-CONF | H2O | Flu A (H1N1) | California/07/ 2009 | MDCK | µg/ml | 3 | 0.07 | | >100 | >1400 |
| 09-001329 | Neutral Red | H2O | Flu A (H3N2) | Brisbane/10/ 2007 | MDCK | µg/ml | 1 | >100 | | >100 | 0 |
| 09-001329 | Visual | H2O | Flu A (H3N2) | Brisbane/10/ 2007 | MDCK | µg/ml | 1 | >100 | | >100 | 0 |
| 09-001330 | Neutral Red | H2O | Flu A (H1N1) | California/07/ 2009 | MDCK | µg/ml | 1 | 2.8 | | >100 | >36 |
| 09-001330 | Visual | H2O | Flu A (H1N1) | California/07/ 2009 | MDCK | µg/ml | 1 | 5.6 | | >100 | >18 |
| 09-001330 | Neutral Red | H2O | Flu A (H1N1) | California/07/ 2009 | MDCK | µg/ml | 2 | 2.7 | | >100 | >37 |
| 09-001330 | Visual | H2O | Flu A (H1N1) | California/07/ 2009 | MDCK | µg/ml | 2 | 1.1 | | >100 | >91 |
| 09-001330 | Virus Yield | H2O | Flu A (H1N1) | California/07/ 2009 | MDCK | µg/ml | 3 | | 17.5 | | >5.7 |
| 09-001330 | Visual-CONF | H2O | Flu A (H1N1) | California/07/ 2009 | MDCK | µg/ml | 3 | 1.1 | | >100 | >91 |
| 09-001330 | Neutral Red | H2O | Flu A (H3N2) | Brisbane/10/ 2007 | MDCK | µg/ml | 1 | 67 | | >100 | >1.5 |
| 09-001330 | Visual | H2O | Flu A (H3N2) | Brisbane/10/ 2007 | MDCK | µg/ml | 1 | 73 | | >100 | >1.4 |
| 09-001331 | Neutral Red | H2O | Flu A (H1N1) | California/07/ 2009 | MDCK | µg/ml | 1 | 6 | | >100 | >17 |
| 09-001331 | Visual | H2O | Flu A (H1N1) | California/07/ 2009 | MDCK | µg/ml | 1 | 5.6 | | >100 | >18 |
| 09-001331 | Neutral Red | H2O | Flu A (H1N1) | California/07/ 2009 | MDCK | µg/ml | 2 | 8.1 | | >100 | >12 |
| 09-001331 | Visual | H2O | Flu A (H1N1) | California/07/ 2009 | MDCK | µg/ml | 2 | 0.9 | | >100 | >110 |
| 09-001331 | Virus Yield | H2O | Flu A (H1N1) | California/07/ 2009 | MDCK | µg/ml | 3 | | <0.3200 | | >310 |
| 09-001331 | Visual-CONF | H2O | Flu A (H1N1) | California/07/ 2009 | MDCK | µg/ml | 3 | 0.9 | | >100 | >110 |
| 09-001331 | Neutral Red | H2O | Flu A (H3N2) | Brisbane/10/ 2007 | MDCK | µg/ml | 1 | >100 | | >100 | 0 |
| 09-001331 | Visual | H2O | Flu A (H3N2) | Brisbane/10/ 2007 | MDCK | µg/ml | 1 | >100 | | >100 | 0 |
| 09-001332 | Neutral Red | H2O | Flu A (H1N1) | California/07/ 2009 | MDCK | µg/ml | 1 | 0.44 | | >100 | >230 |
| 09-001332 | Visual | H2O | Flu A (H1N1) | California/07/ 2009 | MDCK | µg/ml | 1 | 0.56 | | >100 | >180 |
| 09-001332 | Neutral Red | H2O | Flu A (H1N1) | California/07/ 2009 | MDCK | µg/ml | 2 | 0.9 | | >100 | >110 |
| 09-001332 | Visual | H2O | Flu A (H1N1) | California/07/ 2009 | MDCK | µg/ml | 2 | 0.1 | | >100 | >1000 |
| 09-001332 | Virus Yield | H2O | Flu A (H1N1) | California/07/ 2009 | MDCK | µg/ml | 3 | | <0.0320 | | >3100 |
| 09-001332 | Visual-CONF | H2O | Flu A (H1N1) | California/07/ 2009 | MDCK | µg/ml | 3 | 0.1 | | >100 | >1000 |
| 09-001332 | Neutral Red | H2O | Flu A (H3N2) | Brisbane/10/ 2007 | MDCK | µg/ml | 1 | >100 | | >100 | 0 |
| 09-001332 | Visual | H2O | Flu A (H3N2) | Brisbane/10/ 2007 | MDCK | µg/ml | 1 | >100 | | >100 | 0 |
| 09-001333 | Neutral Red | H2O | Flu A (H1N1) | California/07/ 2009 | MDCK | µg/ml | 1 | 2.7 | | >100 | >37 |
| 09-001333 | Visual | H2O | Flu A (H1N1) | California/07/ 2009 | MDCK | µg/ml | 1 | 5.6 | | >100 | >18 |
| 09-001333 | Neutral Red | H2O | Flu A (H1N1) | California/07/ 2009 | MDCK | µg/ml | 2 | 0.3 | | >100 | >330 |
| 09-001333 | Visual | H2O | Flu A (H1N1) | California/07/ 2009 | MDCK | µg/ml | 2 | 0.7 | | >100 | >140 |
| 09-001333 | Virus Yield | H2O | Flu A (H1N1) | California/07/ 2009 | MDCK | µg/ml | 3 | | <0.0332 | | >3100 |
| 09-001333 | Visual-CONF | H2O | Flu A (H1N1) | California/07/ 2009 | MDCK | µg/ml | 3 | 0.7 | | >100 | >140 |
| 09-001333 | Neutral Red | H2O | Flu A (H3N2) | Brisbane/10/ 2007 | MDCK | µg/ml | 1 | 49 | | >100 | >2 |
| 09-001333 | Visual | H2O | Flu A (H3N2) | Brisbane/10/ 2007 | MDCK | µg/ml | 1 | 46 | | >100 | >2.2 |

TABLE 3-continued

Effects of sulfated polysaccharides on viral strains

| ARB # | Assay | Vehicle | Virus | Strain | Cell Line | Drug Unit | Trial | EC50 | EC90 | IC50 | SI |
|---|---|---|---|---|---|---|---|---|---|---|---|
| 09-001334 | Neutral Red | H2O | Flu A (H1N1) | California/07/ 2009 | MDCK | µg/ml | 1 | 0.3 | | >100 | >330 |
| 09-001334 | Visual | H2O | Flu A (H1N1) | California/07/ 2009 | MDCK | µg/ml | 1 | 0.56 | | >100 | >180 |
| 09-001334 | Neutral Red | H2O | Flu A (H1N1) | California/07/ 2009 | MDCK | µg/ml | 2 | 2.7 | | >100 | >37 |
| 09-001334 | Visual | H2O | Flu A (H1N1) | California/07/ 2009 | MDCK | µg/ml | 2 | 0.07 | | >100 | >1400 |
| 09-001334 | Virus Yield | H2O | Flu A (H1N1) | California/07/ 2009 | MDCK | µg/ml | 3 | | <0.0320 | | >3100 |
| 09-001334 | Visual-CONF | H2O | Flu A (H1N1) | California/07/ 2009 | MDCK | µg/ml | 3 | 0.07 | | >100 | >1400 |
| 09-001334 | Neutral Red | H2O | Flu A (H3N2) | Brisbane/10/ 2007 | MDCK | µg/ml | 1 | >100 | | >100 | 0 |
| 09-001334 | Visual | H2O | Flu A (H3N2) | Brisbane/10/ 2007 | MDCK | µg/ml | 1 | >100 | | >100 | 0 |

Example 3

Applications

A method is provided for inhibiting a virus of the orthomyxoviridae family or a condition or symptom associated with orthomyxoviral infection. The method comprises contacting the virus or a cell infected with the virus with an effective amount of a formulation comprising a sulfated polysaccharide having an average molecular weight of about 4,000 Daltons, such as from about 4,000 Daltons to about 5 million Daltons.

The formulation includes a formulation comprising the sulfated polysaccharide at a concentration of from about 1% w/w to 100% w/w. Examples of sulfated polysaccharides include fucan sulfate, galactofucan sulfate, other fucose-rich sulfated polysaccharides, a rhamnose-containing sulfated polysaccharide, chondroitin sulfate, heparin sulfate and glycosaminoglycan. In an embodiment, the sulfated polysaccharide is fucoidan or a physically, chemically and/or enzymatically derivatized form thereof.

A virus of the orthomyxoviridae family includes an influenza virus of species Influenza A, Influenza B and/or Influenza C or a sub-type or variant thereof. Examples of Influenza A is sub-type $H_xN_y$, wherein $H_x$ is a hemagglutinin of type 1 to 9 inclusive and $N_y$ is a neuraminidase of type 1 to 16 inclusive, such as sub-types $H_1N_1$, $H_1N_2$, $H_3N_1$, $H_3N_2$, $H_2N_3$, $H_5N_1$, $H_7N_3$, $H_7N_7$ and $H_9N_2$.

In a particular embodiment, the virus is swine flu virus or avian flu virus, such as strains which infect humans.

Also taught herein is an ability for the sulfated polysaccharide to reduce the effects of cytokine and growth factor production. The sulfated polysaccharide may be given alone or in combination with another anti-viral agent such as oseltamivir (tamiflu), zanamivir (relenza), amantadine or a cytokine such as γ-interferon.

Further enabled herein is a use of a sulfated polysaccharide in the manufacture of a medicament for the treatment or control of influenza virus infection or conditions associated with viral infection. Contemplated is a use of an extract from brown seaweed or a green seaweed comprising a sulfated polysaccharide having an average molecular weight of from about 4,000 Daltons to about 5 million Daltons in the manufacture of a medicament or functional food for the treatment or control of influenza virus infection.

Examples of the influenza virus include swine and avian flue viruses. The present disclosure also teaches a method for reducing flu-like symptoms associated with infection by an influenza virus, the method comprising administering to a subject an effective amount of a sulfated polysaccharide having an average molecular weight of 4,000 Daltons or greater, such as from about 4,000 Daltons to about 5 million Daltons.

Those skilled in the art will appreciate that the subject matter described herein is susceptible to variations and modifications other than those specifically described. It is to be understood that the disclosure includes all such variations and modifications to the subject matter. The disclosure contemplates all of the steps, features, compositions and compounds referred to or indicated in this specification, individually or collectively, and any and all combinations of any two or more of these steps, features, compositions and/or compounds.

BIBLIOGRAPHY

Berteau and Mulloy, *Glycobiology* 13(6):29-40, 2003
Bouvier and Palese, *Vaccine* 26 *Suppl.* 4:D49-53, 2008
deZong et al, *Clinical Chemistry* 35(7):1472-1477, 1981
Harder and Ortrud, *Influenza Report, Chapter* 2, 2006
Heinen, *Veterinary Science Journal,* 15 Sep. 2009
Irhimeh et al, *Methods Fnd Exp. Clin. Pharmacol.* 27(10): 705-710, 2005
Leong et al, *Ann Acad Med Sngap* 37(6):504-509, 2008
Presti et al, *J. Virol.* 83(22):11599-11606, 2009
Scott and Darling, *Histochemic* 5:221-233, 1965

The invention claimed is:

1. A method for inhibiting a virus of the Orthomyxoviridae family or treating an infection with a virus of the Orthomyxoviral family, said method comprising:
    contacting the virus or a cell infected with the virus with an effective amount of a formulation selected from Formulation A and Formulation B, the formulation comprising a total fucoidan content provided by fucoidan molecules as defined by the following molecular weight ranges and levels in Formulation A or Formulation B:
    Formulation A comprising:
    (i) less than 5 kDa present at a level of about 9.8% (w/w);
    (ii) 5-20 kDa present at a level of about 2.2% (w/w);
    (iii) 20-60 kDa present at a level of about 8.4% (w/w);

(iv) 60-200 kDa present at a level of about 18.6% (w/w);
(v) 200-1100 kDa present at a level of about 32.3% (w/w);
(vi) 1100-1600 kDa present at a level of about 6.3% (w/w); and
(vii) greater than 1600 kDa present at a level of about 22.4% (w/w), and Formulation B comprising:

i) less than 5 kDa present at a level of about 11.1% (w/w);
(ii) 5-20 kDa present at a level of about 6.8% (w/w);
(iii) 20-60 kDa present at a level of about 15.5% (w/w);
(iv) 60-200 kDa present at a level of about 24.2% (w/w);
(v) 200-1100 kDa present at a level of about 22.8% (w/w);
(vi) 1100-1600 kDa present at a level of about 2.5% (w/w); and
(vii) greater than 1600 kDa present at a level of about 17.1% (w/w), wherein any fucoidan molecule of the formulation is in a naturally occurring form, or a physically, chemically, and/or enzymatically derivatized form thereof.

2. The method of claim 1 wherein the virus is an influenza sub-type A $H_1N_1$ virus, or an influenza sub-type A $H_3N_2$ virus.

3. The method of claim 1 further comprising the administration of an anti-viral agent selected from oseitamivir (tamiflu), zanamivir (relenza), am